United States Patent [19]

Takeuchi et al.

[11] Patent Number: 5,622,738

[45] Date of Patent: Apr. 22, 1997

[54] METHOD OF PREPARING WATER-SOLUBLE DIETARY FIBER

[75] Inventors: Masayasu Takeuchi; Masayoshi Sugawara, both of Fuji; Seishiro Kainuma, Shimizu; Nobuyuki Nakamura, Mishima; Mikio Yamamoto, Fuji, all of Japan

[73] Assignee: Nihon Shokuhin Kako Co., Ltd., Tokyo, Japan

[21] Appl. No.: 406,774

[22] Filed: Mar. 17, 1995

Related U.S. Application Data

[63] Continuation of Ser. No. 130,155, Sep. 30, 1993, abandoned, which is a continuation of Ser. No. 849,794, Mar. 11, 1992, abandoned, which is a continuation of Ser. No. 516,434, Apr. 30, 1990, abandoned.

[30] Foreign Application Priority Data

May 16, 1989 [JP] Japan ..................................... 1-121877
Jul. 18, 1989 [JP] Japan ..................................... 1-185698

[51] Int. Cl.⁶ ..................................... A23B 7/00
[52] U.S. Cl. ................................ 426/52; 426/18; 426/49; 426/648
[58] Field of Search ................................. 426/48, 52, 64, 426/18, 20, 21, 49, 648, 615, 618

[56] References Cited

U.S. PATENT DOCUMENTS

| | | | |
|---|---|---|---|
| 3,574,634 | 4/1971 | Singer | 426/64 |
| 3,983,002 | 9/1976 | Ohya et al. | 435/822 |
| 4,927,654 | 5/1990 | Barnett et al. | 426/548 |
| 4,948,600 | 8/1990 | Zumbé et al. | 426/64 |
| 5,126,143 | 6/1992 | Natashima et al. | 424/439 |

FOREIGN PATENT DOCUMENTS

| | | | |
|---|---|---|---|
| 0254879 | 3/1988 | Germany | 426/52 |
| 254879 | 3/1988 | Germany | 426/52 |
| 13357 | 5/1975 | Japan . | |
| 53-62848 | 5/1978 | Japan | 426/52 |
| 0062848 | 6/1978 | Japan | 426/52 |
| 0025016 | 7/1978 | Japan | 426/52 |
| 53-25016 | 7/1978 | Japan | 426/52 |
| 0041824 | 3/1983 | Japan | 426/52 |
| 58-41824 | 3/1983 | Japan | 426/52 |
| 1689 | 1/1984 | Japan . | |

OTHER PUBLICATIONS

CA 111:41666, Takeuchi, 1989.

*Primary Examiner*—Leslie Wong
*Attorney, Agent, or Firm*—Frishauf, Holtz, Goodman, Langer & Chick, P.C.

[57] ABSTRACT

A water-soluble dietary fiber comprising as a main component a partially hydrolyzed product of a hemicellulose extracted from a vegetable fiber material by an alkali treatment and subjected to enzymolysis. Various kinds of food and drink can be prepared by mixture of this dietary fiber. Also disclosed is a method of preparing a water-soluble dietary fiber, comprising the steps of subjecting a vegetable fiber material to extraction by an alkali treatment, and treating an extract therefrom with a xylanase to give a partially hydrolyzed product of hemicellulose.

7 Claims, No Drawings

METHOD OF PREPARING WATER-SOLUBLE DIETARY FIBER

This application is a continuation of application Ser. No. 08/130,155 filed Sep. 30, 1993, now abandoned which is a continuation of application Ser. No. 07/849,794 filed Mar. 11, 1992, now abandoned, which is a continuation of application Ser. No. 07/516,434 filed Apr. 30, 1990 now abandoned.

FIELD OF THE INVENTION

The present invention relates to a water-soluble dietary fiber mainly composed of hemicellulose extracted from dietary fiber materials such as hulls of grains, malt roots, and wood, food and drink containing the water-soluble dietary fiber, and a method of preparing the water-soluble dietary fiber.

BACKGROUND OF THE INVENTION

In recent years, dietary fibers have attracted notice as health foods. The dietary fibers are mainly composed of cellulose, hemicellulose, lignin, pectin and so forth. They are distinguished from so-called crude fibers conventionally available, and regarded as hardly digestible vegetable components contained in vegetable cell walls and inclusions contained in grains or the like. Hulls of grains or beans, including corn bran, wheat bran and rice bran, have attracted notice as sources of such dietary fibers. These are progressively acknowledged to have a correlation to an increase or decrease in serum cholesterol, prevention of corpulence and diabetes, appendicitis, and promotion of the elimination of poisonous substances in food. The hulls of grains or beans, however, have the disadvantages that they are not soluble in water unless treatment is applied and, when eaten, also give an unpleasant feeling even if they are finely powdered.

For these reasons, it has been attempted to extract hemicellulose from the hulls of grains or beans to obtain water-soluble dietary fibers. Hemicellulose can be extracted by subjecting the hulls of grains or beans to an alkali treatment. The hemicellulose thus extracted is found to exhibit inhibitory action against an increase in serum cholesterol (Japanese Patent Publication No. 1689/1984).

The hemicellulose obtained by alkali extraction, however, gives a considerably high viscosity when it is dissolved in water even in a small amount, and hence it has been disadvantageous in that when used, for example, in drink preparations it tends to give an unpleasant sensation when swallowing, and some difficulties are brought about also in preparation steps including filtration.

It was also attempted to obtain water-soluble dietary fibers by subjecting hulls of grains or beans to acid treatment or explosive crushing. These methods, however, result in hydrolysis of the hemicellulose to a monosaccharide or an oligosaccharide, and thus have the problem that the resulting products can no longer be said to be dietary fibers.

SUMMARY OF THE INVENTION

Accordingly, an object of the present invention is to provide a water-soluble dietary fiber that can give a low viscosity when dissolved in water.

Another object of the present invention is to provide food and drink containing a water-soluble dietary fiber so that a good sensation when swallowing can be maintained, in particular, in drink preparations or the like.

Still another object of the present invention is to provide a method of preparing in an industrial scale the above water-soluble dietary fiber from vegetable fiber materials such as hulls of grains.

The present inventors made intensive studies to achieve the above objects. As a result, they have found that a dietary fiber obtained by partial hydrolysis of the hemicellulose extracted from a dietary fiber material by an alkali treatment can give a relatively low viscosity when dissolved in water, and yet retain the properties inherent in dietary fibers. They have thus accomplished the present invention on the basis of such findings.

Stated summarily, the water-soluble dietary fiber of the present invention is mainly composed of a partially hydrolyzed product of a hemicellulose extracted from a vegetable fiber material by an alkali treatment and subjected to enzymolysis.

The food and drink of the present invention is characterized by containing a partially hydrolyzed product of a hemicellulose extracted from a vegetable fiber material by an alkali treatment and subjected to enzymolysis.

The method of preparing the water-soluble dietary fiber of the present invention is characterized by comprising the steps of subjecting a vegetable fiber material to extraction by an alkali treatment, and treating an extract therefrom with a xylanase to give a partially hydrolyzed product of a hemicellulose.

The water-soluble dietary fiber of the present invention is a water-soluble dietary fiber mainly composed of a hemicellulose extracted from a vegetable fiber material by an alkali treatment, followed by treatment with a xylanase, which hemicellulose has been made low-molecular and cut into block units in an appropriate degree. This hemicellulose has not been made low-molecular to the level of monosaccharides or oligosaccharides, and hence it can retain a physiological activation function as a dietary fiber. Moreover, since it is water-soluble and gives a low viscosity when added in water, it can be readily added in food and drink. In particular, since it gives a low viscosity when added in drink, a good sensation when swallowing can be obtained even if it has been added in a relatively large amount. It is therefore possible for the water-soluble dietary fiber of the present invention to be applied in a vast range of food and drink including bread, cake, crackers and cookies, as well as juice, lactic acid drinks, sauce, soup, and drink preparations. The achievement of a low viscosity as mentioned above also makes it easy to carry out preparation steps including filtration.

DESCRIPTION OF THE PREFERRED EMBODIMENTS

The present invention will be described below in greater detail by giving preferred embodiments.

In the present invention, waste agricultural and forestry materials containing xylans, such as hulls of grains, malt roots, and wood may preferably be used as the vegetable fiber material. More preferably used are those prepared by removing starch, proteins, lipids, minerals, etc. from the above materials, i.e., those mainly composed of cellulose and hemicellulose, and containing a small amount of lignin. Here, for example, corn hulls, rice bran, wheat bran, and barley bran may preferably be used as the hulls of grains.

As methods of removing starch, proteins, lipids, minerals, etc. from the materials such as hulls of grains, malt roots, and wood, an enzymatic treatment, a chemical treatment, a physical treatment and so forth can be employed. These may also be employed in combination for the treatment.

The enzymatic treatment includes, for example, a method in which the treatment is carried out by causing a starch lytic enzyme such as α-amylase or glucoamylase, a lipid lytic enzyme such as lipase, or fiber lytic enzyme such as cellulase to act on the material under conditions of a pH of from 3 to 9 and a temperature of from 30 to 100. The chemical treatment includes a method in which an aqueous solution of a mineral acid or an organic acid is added to the material and the resulting mixture is heated under conditions of pH 2 to 5, and a method in which a surface active agent used for food is added to the material and the resulting mixture is heated under conditions of pH 3 to 8. The physical treatment includes, for example, a method in which the material is pulverized with a pulverizer such as a homogenizer or a hammer mill, followed by sieving.

The method of subjecting the vegetable fiber material to extraction by an alkali treatment can be carried out by any known methods. For example, the vegetable fiber material as described above is suspended in an aqueous solution of an alkali such as sodium hydroxide or calcium hydroxide, and the resulting suspension may be treated at a given temperature for a given time. As a preferred example, 0.8 part by weight of calcium hydroxide and 1,000 parts by weight of water are added to 100 parts by weight of the vegetable fiber material, and the resulting mixture is treated at 125° C. for 15 minutes. Hemicellulose can be thus extracted.

The extract solution thus obtained by the alkali treatment is cooled preferably to 50° C. to 60° C., the pH of which is then optionally adjusted with sulfuric acid, hydrochloric acid or the like, followed by addition of xylanase to carry out reaction. The xylanase may preferably be added in an amount of about 0.001 unit to about 10 units per gram of the solid content of the extract. The reaction may preferably be carried out for about 3 hours to about 96 hours. The titer of xylanase may be measured in the following way: The amount of the enzyme that produces a reducing sugar corresponding to 1 micromole of xylose in 1 minute under reaction conditions of pH 7 and 60° C. using as a substrate a hemicellulose extracted from corn by the alkali treatment, is regarded as 1 unit.

The xylanase used in the present invention may more preferably be that of a liquefied type than that of a saccharified type. It may be the one originating from fungi or the one originating from bacteria, either of which can be used. The xylanase originating from bacteria may however be more preferred because of its higher purity.

The optimum pH at which the xylanase acts ranges from the acid side to the alkaline side, and a xylanase of either pH side can be used under adjustment of the pH as occasion calls. On account of the fact that the extract is alkaline, it is more preferred to use an alkaline xylanase having the optimum pH at the alkaline side. Such an alkaline xylanase includes, for example, xylanases as disclosed in Japanese Patent Publication No. 13357/1975.

While usual xylanases have the optimum pH at the acid side of pH 4 to 5, the alkaline xylanase acts at a wide pH range of from neutral to alkaline. Hence, it does not require any pH adjustment after the extraction by the alkali treatment, or may only require use of acid in a small amount. It also has a strong heat resistance, and hence is easy to use.

In the present invention, besides the usual xylanase and the alkaline xylanase, as described above, a commercially available cellulase containing a xylanase may also be used alone or in combination with the above xylanase. For example, in a cellulase produced by Genencor Co., an activity as the xylanase is also observed, and hence it can be used as the xylanase in the present invention.

A reaction mixture thus obtained by causing the xylanase to react in the alkali-treatment extract solution may, for example, be heated to deactivate the enzyme, which is then subjected to solid-liquid extraction by centrifugal separation or the like, followed by clarification purification if necessary, and further followed by decoloring, desalting, concentration, and drying. The water-soluble dietary fiber mainly composed of a partially hydrolyzed product of the hemicellulose can be thus obtained.

Alternatively, an extract obtained by the alkali treatment of the vegetable fiber material may be subjected to solid-liquid extraction, followed by clarification purification, thereafter adjustment of the pH, treatment with xylanase, deactivation of the enzyme, decoloring, desalting, concentration, and drying.

The former method, in which the material is treated with the xylanase immediately after the alkali treatment, can bring about a low viscosity of the reaction mixture, making it easy to carry out the solid-liquid extraction and the operations subsequent thereto. Thus, there is the advantage that an extract solution with a high viscosity can be recovered in a good efficiency. The latter method, in which the material is subjected to solid-liquid extraction and then treated with the xylanase, has the advantage that the pH can be readily adjusted and only a small amount of enzyme is required.

The water-soluble dietary fiber of the present invention, thus obtained, is mainly composed of the partially hydrolyzed product of a hemicellulose, and contains 80% or more of dietary fibers when measured by, for example, the Prosky et al's method [Prosky, L., et al., J. Assoc. Off. Anal. Chem., 67, 1044, (1984), J. Assoc. Off. Anal. Chem., 68, 399 (1985)] (AOAC Prosky method). Hence, a superior effect of physiological activation can be promised with its use in a small amount. When it has been dissolved in water, the viscosity can be kept at a very low level, compared with conventional water-soluble dietary fibers. In this connection, an aqueous 5% solution of a hemicellulose obtained by only the alkali extraction has a viscosity of from 50 to 110 cps when measured using a B-type (Brookfield) viscometer at 60 rpm and 25° C. On the other hand, an aqueous 5% solution of the hemicellulose obtained by subjecting the above hemicellulose to the enzymatic treatment to effect partial hydrolysis has a viscosity of from 5 to 20 cps when measured in the same manner as in the above.

The food and drink containing the water-soluble dietary fiber of the present invention are obtained by adding the partially hydrolyzed product of a hemicellulose, obtained in the above way, in food and drink such as juice, lactic acid drinks, ice cream, jelly, bread, and cookies. Since it is water-soluble and can give a low viscosity when dissolved in water, there are no limitations on the kinds of the food and drink, and it can be added in almost all kinds of food and drink.

The partially hydrolyzed product of hemicellulose may preferably be added in the food and drink in an amount of from 0.5 to 10% by weight. Addition thereof in an amount less than 0.5% can not promise the physiological activation function for dietary fibers, such as the inhibitory effect against an increase in serum cholesterol. Addition thereof in an amount more than 10% by weight may sometimes result in an increase in the viscosity of drink, or a loss of flavour, or feeling of eating, of food. In particular, in the case of the drink such as juice or lactic acid drink, the above partially hydrolyzed product of the present invention may preferably be added in an amount of from 0.5 to 5% by weight; and in the case of the solid food such as bread or cookies, in an amount of from 0.5 to 10% by weight.

EXAMPLES

The present invention will be described below in more greater detail by giving Examples, to which, however, the present invention is by no means limited.

Example 1

To 100 parts by weight of corn hulls, 1,000 parts by weight of water and 1 part by weight of calcium hydroxide were added, and the mixture was heated at 85° C. for 3 hours, followed by cooling to 60° C., and adjustment of the pH to 7 by adding sulfuric acid. Subsequently, an alkaline xylanase was added in an amount of 0.01 unit per gram of the solid content of the reaction mixture, and the reaction was carried out for 48 hours. The alkaline xylanase used was prepared in the same manner as the one disclosed in Japanese Patent Publication No. 13357/1975.

The alkaline xylanase used was prepared in the following manner:

In 900 ml of water, 10 g of rice straw xylane, 10 g of peptone, 5 g of yeast extract, 1 g of $K_2HPO_4$ and 0.1 g of $MgSO_4$ were dissolved, and the solution was sterilized at 115° C. for 15 minutes. Thereafter, 100 ml of a 10% $Na_2CO_3$ previously sterilized in a separate system was added thereto to give a culture solution.

This culture solution was taken in an amount of 100 ml, and pipetted into a 1 lit. Erlenmeyer flask. Into the culture solution, a strain of Bacillus sp. No. C-59-2 (FERM No. 1698) was inoculated in the amount of a platinum loop, followed by shaken culture at 37° C. for 48 hours. Thereafter, bacterial bodies were removed by centrifugal separation.

To the resulting supernatent, alcohol was added to effect precipitation of xylanase, and the precipitate was collected by centrifugal separation. The resulting precipitate was freeze-dried to give a dry powder of alkaline xylanase. Next, the reaction mixture was heated at 90° C. for 30 minutes to deactivate the enzyme, followed by solid-liquid extraction, clarification filtration, decoloring, and desalting to effect purification. The purified product was dried with a spray dryer to give a powder. The resulting powder was measured by the Prosky et al's method to reveal that it contained 85% of total dietary fiber.

Example 2

To 100 parts by weight of corn hulls, 1,000 parts by weight of water and 0.8 part by weight of calcium hydroxide were added, and the mixture was heated at 125° C. for 15 minutes, followed by cooling, addition of 500 parts by weight of hot water, and then solid-liquid extraction by centrifugal separation to give a filtrate. Subsequently, the filtrate was adjusted to pH 5.5, and 0.1% of cellulase (a product of Genenco Co.) to the resulting filtrate, and the reaction was carried out at 50° C. for 24 hours to give a reaction mixture. The enzyme in the reaction mixture was deactivated, followed by purification in the same manner as in Example 1, and drying to give a powder of dietary fibers.

Next, tests were made to examine the decrease of viscosity, attributable to the enzymatic treatment in Examples 1 and 2.

(1) Measurement of Viscosity of Slurry:

In Example 1, after the starting material was subjected to alkali extraction, the viscosity of the reaction mixture before its treatment with the alkaline xylanase and that of the reaction mixture after the treatment were measured in the following manner.

The tip of a 10 ml measuring pipette was cut away and the sample was sucked up. Thereafter, the time taken for 5 ml of sample to move at room temperature was measured. Results obtained are shown in Table 1.

TABLE 1

| Before treatment with alkaline xylanase: | 126 sec. |
|---|---|
| After treatment with alkaline xylanase: | 20.4 sec. |

Thus, the viscosity is seen to decrease as a result of the treatment with alkaline xylanase.

(2) Measurement of Filtering Properties:

Example 2 was repeated to subject the starting material to alkali extraction. Thereafter, various enzymes, alkaline xylanase, cellulase (a product of Genecon Co.), α-amylase and neutral protease, were each added to the filtered solution, and the reaction was carried out overnight under an optimum pH at 50° C. As a comparative example, also prepared was a control in which no enzyme was added. Each reaction mixture was collected in a portion of 10 ml, which was then filtered for 2 minutes using a millipore filter (4.9 $cm^2$) with a pore size of 0.45 μm, and the amount of a filtrate was measured. Results obtained are shown in Table 2.

TABLE 2

| Enzyme added | Amount of filtrate |
|---|---|
| Control | 0.1 ml |
| Alkaline xylanase | 10 ml |
| Cellulase | 10 ml |
| α-Amylase | 1.0 ml |
| Neutral protease | 1.0 ml |

Thus, the filtering properties is seen to be greatly improved as a result of the treatment of the filtrate with alkaline xylanase or cellulase.

(3) Viscosity of Product:

The dietary fibers prepared in Example 2, and dietary fibers prepared in the same manner as in Example 2 except that the enzymatic treatment was not carried out, were each dissolved in water to give a concentration of 5%, and the viscosity in each aqueous solution at 50° C. was measured using a Brookfield viscometer at 25° C. (60 rpm). Results obtained are shown in Table 3.

TABLE 3

| Aqueous solution | Viscosity |
|---|---|
| dietary fibers with no enzymatic treatment | 37.5 cps |
| dietary fibers of Example 2 | 2.0 cps |

Thus, the viscosity of the product is seen to greatly decrease as a result of the enzymatic treatment.

Next, various kinds of food and drink were prepared using the water-soluble dietary fiber obtained in Example 1. In the following Examples, "part(s)" and "%" are parts by weight and % by weight, respectively, unless particularly mentioned.

Example 3

On commercially available 100% orange juice, 3 g of the water-soluble dietary fiber obtained in Example 1 (hereinafter "water-soluble dietary fiber") was dissolved to prepare fruit juice.

| (Mixing composition) | |
| --- | --- |
| 100% Orange juice | 100 parts |
| Water-soluble dietary fiber | 3 parts |

This juice was sampled to confirm that it tasted mildly sour and was found to be fruit juice with a good flavor.

Example 4

In an aqueous 5% solution of the water-soluble dietary fiber, first-class red fresh bean paste, granulated sugar, and water were added to give the following mixing composition, and the mixture was kneaded with heat-stirring until it has a Bx concentration of 60. A bean paste was thus prepared.

| (Mixing composition) | |
| --- | --- |
| First-class red fresh bean paste | 300 parts |
| Granulated sugar | 200 parts |
| Water | 100 parts |
| Aqueous 5% water-soluble dietary fiber | 100 parts |

The product was sampled to confirm that the bean paste had a good gloss and flavor.

Example 5

Using an aqueous 2% water-soluble dietary fiber, strawberry jelly was prepared to have the following mixing composition.

| (Mixing composition) | |
| --- | --- |
| Gelatin | 12 parts |
| Aqueous 2% water-soluble dietary fiber | 300 parts |
| Sugar | 80 parts |
| Strawberry juice | 150 parts |

The product was sampled to confirm that it had a good eating feeling and flavor.

Example 6

The water-soluble dietary fiber was dissolved in vinegar to prepare French dressing with the following mixing composition.

| (Mixing composition) | |
| --- | --- |
| Water-soluble dietary fiber | 2 parts |
| Vinegar | 100 parts |
| Oil | 100 parts |
| Salt | 10 parts |
| Pepper | 2 parts |

The addition of the water-soluble dietary fiber brought about an increase in the stability of the dressing, and was also found that it adhered to vegetables in an increased amount.

Example 7

The water-soluble dietary fiber was dissolved in raw hen's eggs to prepare a base material with the following mixing composition, which was then baked in an oven of 170° C. to make sponge cake.

| (Mixing composition) | |
| --- | --- |
| Water-soluble dietary fiber | 5 parts |
| Hen's eggs | 140 parts |
| Sugar | 60 parts |
| Wheat flour | 100 parts |
| Corn starch | 40 parts |
| Butter | 30 parts |

As a result, sponge cake with a fine texture and rich volume was obtained.

Example 8

The water-soluble dietary fiber was dissolved in cow's milk, to which sugar was added and dissolved with heating. Gelatin which had been swollen by immersion in water was hydro-extracted and then mixed in the solution. The resulting mixture was put in a container, and floated on cold water so that it was cooled. Thereafter, the cooled product was put in a refrigerator until it turned into a semisolid. Then, fresh cream was added to the semisolid product, followed by stirring for a while. Ice cream was thus prepared.

| (Mixing composition) | |
| --- | --- |
| Water-soluble dietary fiber | 10 parts |
| Cow's milk | 210 parts |
| Sugar | 75 parts |
| Gelatin | 2 parts |
| Fresh cream | 90 parts |

The ice cream was sampled to confirm that it was smooth and had a superior eating feeling.

Example 9

Using a domestic noodle-maker, noodles with the following mixing composition were prepared, and then boiled to give boiled noodles.

| (Mixing composition) | |
| --- | --- |
| Wheat flour | 100 parts |
| Sodium chloride | 2 parts |
| Water-soluble dietary fiber | 1 part |
| Water | 30 parts |

The resulting boiled noodles had a good flavor and crisp texture, and tasted good with a comfortable hardness.

Example 10

Corn potage with the following mixing composition was prepared.

| (Mixing composition) | |
| --- | --- |
| Corn | 500 parts |
| Onion | 100 parts |
| Butter | 60 parts |
| Wheat flour | 80 parts |
| Soup stock | 1,000 parts |
| Cow's milk | 1,000 parts |
| Salt | 20 parts |
| Water-soluble dietary fiber | 20 parts |
| Pepper | an appropriate amount |
| Chemical condiment | an appropriate amount |

The resulting product was sampled to confirm that it was soup with a smoothness and a good flavor.

Example 11

Butter rolls with the following mixing composition were prepared.

| (Mixing composition) | |
| --- | --- |
| Wheat flour | 300 parts |
| Dry yeast | 7.5 parts |
| Sugar | 3 parts |
| Hot water (40° C.) | 50 parts |
| Water-soluble dietary fiber | 5 parts |
| Sugar | 30 parts |
| Sodium chloride | 4.5 parts |
| Cow's milk | 100 parts |
| Egg | $ |
| Butter | 30 parts |

The resulting butter rolls had a little superior texture and gloss than conventional products, and had little change in flavor.

What is claimed is:

1. A method of preparing a water-soluble dietary fiber, comprising the steps of:

(a) treating a vegetable fiber material with an alkali, (b) extracting from the treated material from step (a) only a liquid component and (c) treating said liquid component with an alkaline xylanase originating from a bacterium to carry out an enzymolysis and to obtain a partially hydrolyzed product of a hemicellulose so that an aqueous 5% solution of the resultant treated hemicellulose has a viscosity from 5 to 20 cps when measured using a Brookfield viscometer at 60 rpm and 25° C. and wherein the dietary fiber is contained in an amount of not less than 80% as measured by the AOAC Prosky method.

2. The method of preparing a water-soluble dietary fiber according to claim 1, wherein said vegetable fiber material is selected from the group consisting of corn hulls, rice bran, wheat bran, barley bran, malt roots, and wood.

3. The method of preparing a water-soluble dietary fiber according to claim 1, wherein said vegetable fiber material is selected from the group consisting of corn hulls, rice bran, wheat bran, barley bran, malt roots, and wood, from which starch, proteins, lipids and minerals have been removed.

4. The method of preparing a water-soluble dietary fiber according to claim 1, said partially hydrolyzed product is further subjected to decoloring, desalting, concentration, and drying.

5. The method according to claim 1, wherein said alkali treatment comprises suspending 100 parts by weight of said vegetable fiber material in 0.8 parts by weight of an alkali selected from the group consisting of sodium hydroxide and calcium hydroxide in 1,000 parts by weight of water at a temperature of 125° C. for 15 minutes.

6. The method according to claim 2, wherein 0.001 to 10 units of said xylanase are utilized per gram of solid content of the resultant extract and said enzymolysis is conducted for a period of 3 hours to 96 hours.

7. The method according to claim 6, wherein the vegetable fiber material is corn hulls.

\* \* \* \* \*